United States Patent
Yue et al.

(10) Patent No.: US 9,533,301 B2
(45) Date of Patent: Jan. 3, 2017

(54) MECHANICAL CELL WOUNDER DEVICE AND RELATED METHOD

(75) Inventors: Ying Kit Yue, Sai Wan (HK); Pui Yin Leung, Shatin (HK); Nai Ki Mak, Kowloon (HK); Ricky Ngok Shun Wong, Shatin (HK)

(73) Assignee: Hong Kong Baptist University, Hong Kong (HK)

( * ) Notice: Subject to any disclaimer, the term of this patent is extended or adjusted under 35 U.S.C. 154(b) by 332 days.

(21) Appl. No.: 11/888,706

(22) Filed: Aug. 2, 2007

(65) Prior Publication Data

US 2009/0035844 A1 Feb. 5, 2009

(51) Int. Cl.
| | | |
|---|---|---|
| *C12M 1/00* | (2006.01) | |
| *B01L 3/02* | (2006.01) | |
| *C12M 1/26* | (2006.01) | |
| *B01L 9/00* | (2006.01) | |

(52) U.S. Cl.
CPC ............. *B01L 3/0244* (2013.01); *C12M 33/04* (2013.01); *B01L 9/54* (2013.01); *B01L 2200/022* (2013.01); *B01L 2200/023* (2013.01); *B01L 2300/0829* (2013.01)

(58) Field of Classification Search
CPC ...... B26B 5/008; B26B 25/007; B26B 25/005; A61B 2017/3405; A61B 17/34; A61B 2017/3409; B01L 3/0244; B01L 9/54; B01L 2200/023; B01L 2300/0829; B01L 2200/022; C12M 1/265
USPC ........ 435/309.1, 283.1, 309.3; 422/925, 927, 422/934, 100; 600/569, 570
See application file for complete search history.

(56) References Cited

U.S. PATENT DOCUMENTS

| | | | | |
|---|---|---|---|---|
| 3,045,348 A | * | 7/1962 | Dungan ................. | A22C 9/008 30/293 |
| 4,601,708 A | * | 7/1986 | Jordan .......................... | 604/136 |
| 6,197,261 B1 | * | 3/2001 | Linville ............... | B01L 3/0293 422/561 |
| 6,274,088 B1 | * | 8/2001 | Burbaum ............... | B01D 61/18 422/503 |
| 6,309,818 B1 | * | 10/2001 | Malinda et al. ................. | 435/4 |

(Continued)

OTHER PUBLICATIONS

Yarrow et al., A high-throughput cell migration assay using scratch wound healing, a comparison of image-based readout method, Sep. 2004, BMC Biotechnology, 4:21 pp. 1-9.*

(Continued)

*Primary Examiner* — William H Beisner
*Assistant Examiner* — Danielle Henkel
(74) *Attorney, Agent, or Firm* — Spruson & Ferguson (Hong Kong) Limited; Sam T. Yip (57) ABSTRACT

Disclosed is a device and related method for biological manipulation. With greater particularity, disclosed is a novel device and method for uniform cellular manipulation with economies of scale and operational uniformity. The device and related method utilize a cellular wounder (101) to uniformly remove portions of a cell monolayer in a multi-well plate (303) to create uniform cell samples with reduced time and expense to the user. The multi-channel mechanical wounder is a useful tool for performing cellular wounding by providing consistent and even denudation of a defined area of monolayer of cells in standard culture plates. This easy-to-assemble and user friendly device is most applicable for high throughput screening of samples such as in the manipulation of cells for cell migration or wound healing assay preparation.

15 Claims, 10 Drawing Sheets

(56) References Cited

U.S. PATENT DOCUMENTS

| | | | |
|---|---|---|---|
| 6,374,683 B1* | 4/2002 | Hunicke-Smith | B01L 3/5085 73/863.32 |
| 6,406,670 B1* | 6/2002 | Earley et al. | 422/553 |
| 7,322,985 B2* | 1/2008 | Lee | A61B 17/148 606/71 |
| 2003/0003025 A1* | 1/2003 | MacAulay et al. | 422/100 |
| 2004/0071602 A1* | 4/2004 | Yiu | 422/100 |

OTHER PUBLICATIONS

Friedl, Peter and Wolf, Katarina, "Tumour-cell invasion and migration: diversity and escape mechanisms". Nat Rev Cancer 2003, 3 (5):362-374.

Friedl, Peter, "Prespecification and plasticity: shifting mechanisms of cell migration". Curr Opin Cell Biol 2004, 16 (1):14-23.

Glaser, Bert M et al., "Adult tissues contain chemoattractants for vascular endothelial cells". Nature 1980, 288 (5790):483-4.

Obeso, Jorge L and Auerbach, Robert, "A new microtechnique for quantitating cell movement in vitro using polystyrene bead monolayers". J Immunol Methods 1984, 70 (2):141-52.

Sholley, Milton M et al., "Cellular migration and replication in endothelial regeneration: a study using irradiated endothelial cultures". Lab Invest 1977, 36 (1):18-25.

Gotlieb, Avrum I and Spector, Wendy, "Migration into an in vitro experimental wound: a comparison of porcine aortic endothelial and smooth muscle cells and the effect of culture irradiation". Am J Pathol 1981, 103 (2): 271-82.

Lampugnani, Maria Grazia, "Cell migration into a wounded area in vitro". Methods Mol Biol 1999, 96:177-182.

Moon, Eun-Joung et al., "A novel angiogenic factor derived from Aloe vera gel: beta-sitosterol, a plant sterol". Angiogenesis 1999, 3 (2):117-23.

Saga, Yasushi et al., "Suppression of cell migration in ovarian cancer cells mediated by PTEN overexpression". Int J Oncol 2003, 23 (4):1109-13.

Liu, Liang et al., "Effects of Si-Jun-Zi decoction polysaccharides on cell migration and gene expression in wounded rat intestinal epithelial cells". Br J Nutr 2005, 93(1):21-29.

Strauch, Eric D et al., "NF-kappaB regulates intestinal epithelial cell and bile salt-induced migration after injury". Ann Surg 2003, 237 (4):494-501.

Vaidya, Rajiv J et al., "MEK1 restores migration of polyamine-depleted cells by retention and activation of Rac1 in the cytoplasm". Am J Physiol Cell Physiol 2005, 288 (2):C350-359.

Rao, Jaladanki N et al., "Differentiated intestinal epithelial cells exhibit increased migration through polyamines and myosin II". Am J Physiol Gastrointest Liver Physiol 1999, 277:G1149-1158.

Miller; Craig A and Debas, Halle T, "Epidermal growth factor stimulates the restitution of rat gastric mucosa in vitro". Exp Physiol 1995, 80 (6):1009-1018.

Brzozowski, Tomasz et al., "Epidermal growth factor, polyamines, and prostaglandins in healing of stress-induced gastric lesions in rats". Dig Dis Sci 1993, 38 (2):276-83.

Wang, Jian-Ying et al., "Role of K(+) channel expression in polyamine-dependent intestinal epithelial cell migration". Am J Physiol Cell Physiol 2000, 278(2):C303-14.

Dignass, Axel U and Podolsky, Daniel K, "Cytokine modulation of intestinal epithelial cell restitution: central role of transforming growth factor beta". Gastroenterology 1993, 105 (5):1323-32.

Yue, Patrick YK et al., "Elucidation of mechanisms underlying the angiogenic effects of ginsenoside Rg1 in vivo and in vitro". Angiogenesis 2005, 8 (3):205-16.

* cited by examiner

MECHANICAL CELL WOUNDER DEVICE AND RELATED METHOD

RELATED APPLICATION

There are no related applications.

TECHNICAL FIELD

The disclosed device and related method relate to the life science field in general as well as to the related biomedical fields which utilize cellular manipulation techniques.

BACKGROUND ART

Manual tools used in cellular manipulation are often single use, single application devices. Mechanical removal of a portion of cell cultures, also known as wounding, results in the physical separation of one or more cells from a cell monolayer. The remaining cells are allowed to recover the area by a process known as reepithelialization. Presently, most of the current techniques for cell removal from a desired cell culture are difficult to perform on a large scale basis in a fast and consistent way when screening for cell migration.

Most of the known cell wounding devices require individual processing in an individual sample well. The repeated application of known cell wounding methods has been used to wound cells to observe total polysaccharides from Si-Jun-Zi decoction in the re-epithelialization of wounded rat intestinal epithelial cells (IEC-6 cells). A similar application of the traditional method of cellular wounding is being applied to observe ginsenoside $Rg_1$ in wounded human umbilical vein endothelial cells (HUVECs).

Apart from the device and related method disclosed herein, there is no known simple method to produce multiple and consistent mechanical wounding of confluent cells for screening of multiple samples. Therefore, a high-throughput wounding method is necessary in order to achieve this goal.

DISCLOSURE OF THE INVENTION

The novel cell wounding device and related method is described in the application of cell wounding on cellular migration. Investigation on cell migration and its underlying mechanism is useful for developing therapeutic drugs since cell migration plays a key role in various normal and pathological activities in organisms. Cell migration assays are usually performed in confluent culture systems by mechanical removal or wounding some part of the cells and allow the cells to reconstruct, also known as wound healing. However, most of the current wounding methods are difficult to perform in large scale screening for potential inducers of cell migration in a fast and consistent way. Manipulating cell monolayer through cell wounding using the claimed device and related method provides uniform and consistent cell removal.

In contrast to conventional wounding devices made of easy to break plastic such as a multi-purpose pipette or generic scraper, the example cellular wounder is made of stainless steel which is highly durable. Most commonly used wounder devices are not amenable to autoclaving due to the plastic nature while the disclosed cellular wounder is autoclavable.

Even more important than durability is consistency of application. With conventional devices it is very difficult to obtain even wounding of cells. In the example device, the adjustable design of the pins which allow even contact with the well surface to achieve simultaneous and even wounds. In the disclosed example, the guiding-bar design ensures consistent wounding position in each well. With previously known devices, it is very common to cause serious mechanical damage to the culture wells when a metal razor blade is using for wounding. Such damages can significantly affect cell migration and image analysis. In contrast to the standard approach, the disclosed device can use standard plastic pipette tips for wounding which provides elasticity to ensure even contact with the well surface but without causing damage to the culture wells. In presently known devices, the chance of cross contamination is relatively higher when using the same wounder such as a razor blade on all cultures. In contrast, the example device use of disposable pipette tips prevents the cross contamination from well to well and facilitates large scale implementation and high throughput screening.

In the use of the disclosed device in the first example, cell migration plays an important role in a variety of normal physiological processes. These include embryogenesis, angiogenesis, wound healing, repairing of intestinal mucosal damage, and immune defense. However, in some pathological conditions such as atherosclerosis or gastrointestinal ulcers, a large area of denudation is commonly found and an immediate repair by re-establishment of intact monolayer of cells is required.

Cell migration is a complex process requiring the coordination of numerous inter-cellular and intra-cellular events, such as cytoskeleton reorganization, matrix remodeling, cell-cell adhesion modulation, as well as induction of chemoattractants. Boyden chamber and phagokinetic assay have been used for a long time in the in vitro study of cell migration. However the induction of cell migration usually involves the response of confluent monolayer cells to mechanical injury, also known as mechanical wounding. These wounds are usually created by the removal of a proportion of confluent cells grown on an individual coverslip or in a multiwell plate using a device such as a pipette tip, razor blade, syringe needle, mechanical scraper, or spatula.

The closure of denuded area which is designated as re-epithelialization, re-endothelialization or wound healing, can then be observed, measured and quantified over a time course using microscopy or computer imaging system. In general, wounding assay is a commonly used method to induce cell migration and its underlying biology such as matrix remodeling or cell polarization. The disclosed device and related method of cell wounding is also useful in angiogenesis, metastasis, and other physiological and pathological biological processes.

Two separate examples are hereby disclosed using an eight-channel mechanical wounder suitable for the 96-well flat bottom plate format. This cellular wounder makes use of disposable plastic pipette tips to produce a uniform denudation of cell monolayer in each well with an average wound size of 600±36.6 μm. The extent of cell migration can be easily quantified by capturing the cell migration images at different time intervals. Using the disclosed cellular wounder and the intestinal epithelial cells (IEC-6) and human umbilical vein endothelial cells (HUVECs) as examples of cellular wounder applications, the effects of restitution under the influence of cell migration enhancer (epithelial growth factor (EGF) or fetal calf serum (FBS)) or inhibitor (alpha-difluoromethylornithine (DFMO), is demonstrated in the 96-well plate. IEC-6 cell is widely used as a cell model in the wounding assay because of its migration property with a classic wound healing response. To mimic the restitution of epithelial damage in the intestine, a monolayer of IEC-6 cells is removed using the cellular wounder and the recovery of denuded area due to cell migration at 16 hours and 24 hours after wounding is depicted. The applicability of the cellular wounder is further represented by introducing substances that can modulate the migration property of IEC-6 cells. DFMO is a well-known inhibitor for cell migration. DFMO inhibits ornithine decarboxylase and decreases the synthesis of polyamines. Since polyamines are required for the early phase of restitution, deficiency in polyamine would affect cell migration. On the other, EGF is used as the inducer of cell migration. In the disclosed wounding system, the IEC-6 cells responded typically to the actions of DFMO and EGF. The percentage of wound closure at 16 hours after wounding is about 60% in control cells while that in EFG-treated cells is enhanced up to more than 90%; and that in DFMO-treated cells decrease to only 33% followed by a further increase in the percentage of wound closure at 24 hours. The percentage of wound closure at 24 hours for control cells is 76% and that in EGF-treated cells is almost 100% whereas in DFMO-treated cells are only around 50%. The enhancing effect of EGF and the inhibitory effect of DFMO on IEC-6 cell migration after 24 hours treatment is clearly demonstrated by the present wounding system. Thus this wounding system can be applied to large scale screening for inducers or inhibitors of cell migration among other situations where precise cellular manipulation is needed. Due to the application of the claimed cellular wounder instead of conventional methods, cellular assay results are more reliable as a result of uniform cellular wounding.

In a second example of the use and benefits of the claimed cellular wounder, the effects of the cellular wounder on HUVECs is also depicted. HUVECs are commonly used in the studying of angiogenesis and wound healing. In the second example, migration of cells is observed at 16 hours and 24 hours after wounding. After use of the claimed wounder, the cells treated with different percentages of fetal bovine serum (0%, 1% and 20%) have different migration rates in concentration-dependent manner for wound healing response. Cells treated with medium alone migrate relatively little with wound closure being less than 40% after 24 hours while cells treated with 20% FBS migrated faster with complete wound closure at 24 hours, whereas cells treated with 1% FBS fall in the intermediate range, with 60% wound closure at 16 hours and 72% wound closure at 24 hours.

In the disclosed first example, IEC-6 cells are seeded at a density of $4 \times 10^4$ cells per well into the 96-well flat-bottomed microtiter plates (Iwaki, code: 3860-096) which are pre-coated overnight with PBS-diluted Matrigel (1:7 (v/v)). After incubation in 10% FBS supplemented DMEM for 24 hours, the cells are starved in serum-free medium for another 24 hours. For wounding of HUVECs, cells are seeded at a density of $3 \times 10^4$ cells per well in gelatin (0.1%) pre-coated 96-well flat-bottomed microtiter plates (Iwaki, code: 3860-096). A cell denuded area is created by scratching the cell monolayer with the eight-channel mechanical wounder fitted with p-10 pipette tips (Axygen, T-300). To ensure even contact between the tips and the bottom of the well, the pins are calibrated by adjusting the hex screw with a hex wrench. With the help of the guiding-bar, the wounder is fixed onto the 96-well plate where each channel (pipette tip) is positioned at the same level in the eight wells of the same column. During wounding, the cell monolayer is scratched by moving the wounder from the left inner edge to the right inner edge of the wells where a sharp wound is formed along the diameter of each well. The wounding procedure is then repeated for all columns of a 96-well plate. After use of the cellular wounder, the medium is replaced with fresh serum-free medium for control wells or with fresh serum-free medium containing 20 ng/ml EGF or 5 mM DFMO for IEC-6 cells, or with different percentages of FBS for HUVECs.

In the description of the drawings, an eight-channel mechanical cell wounder embodiment is disclosed in further detail. Other readily foreseen embodiments include devices with fewer or more channels. The embodiment disclosed describes performing wounding assay in 96-well plate format. The device and related method can provide consistently shaped wounds with uniform size in the same position of each well for easy quantification. The claimed cellular wounder device can be autoclavable, adjustable and easy-to-assemble device that does not require expensive accessories during its application. The pins of the example wounder device are designed to fit disposable p-10 pipette tips. Other tips providing similar functionality can be employed without departing from the spirit and scope of the claimed invention. In the disposable pipette tip embodiment, the use of disposable tips can prevent cross contamination and avoid blunting of the tips due to repeated wounding. In the figures, the disclosed mechanical cellular wounder embodiment and related method is described with respect to migration of IEC-6 and HUVEC cells after wounding.

BRIEF DESCRIPTION OF THE DRAWINGS

FIG. 1 (A) is a front view of an example eight-channel mechanical cellular wounder.

FIG. 1 (B) is a perspective view of an example eight-channel mechanical cellular wounder.

FIG. 4 (A) is a top view of a 96-well plate after application of the eight-channel mechanical cellular wounder.

FIG. 4 (B) is a statistical representation of wound size after device application.

FIG. 5 (A) is a top view of migration of IEC-6 cells after cellular wounding.

FIG. 5 (B) is a statistical representation of cellular migration as a function of wound closure.

FIG. 6 (A) is a top view of migration of HUVECs after cellular wounding.

FIG. 6 (B) is a statistical representation of cellular migration as a function of wound closure.

DETAILED DESCRIPTION OF THE DRAWINGS

Figure 1A:
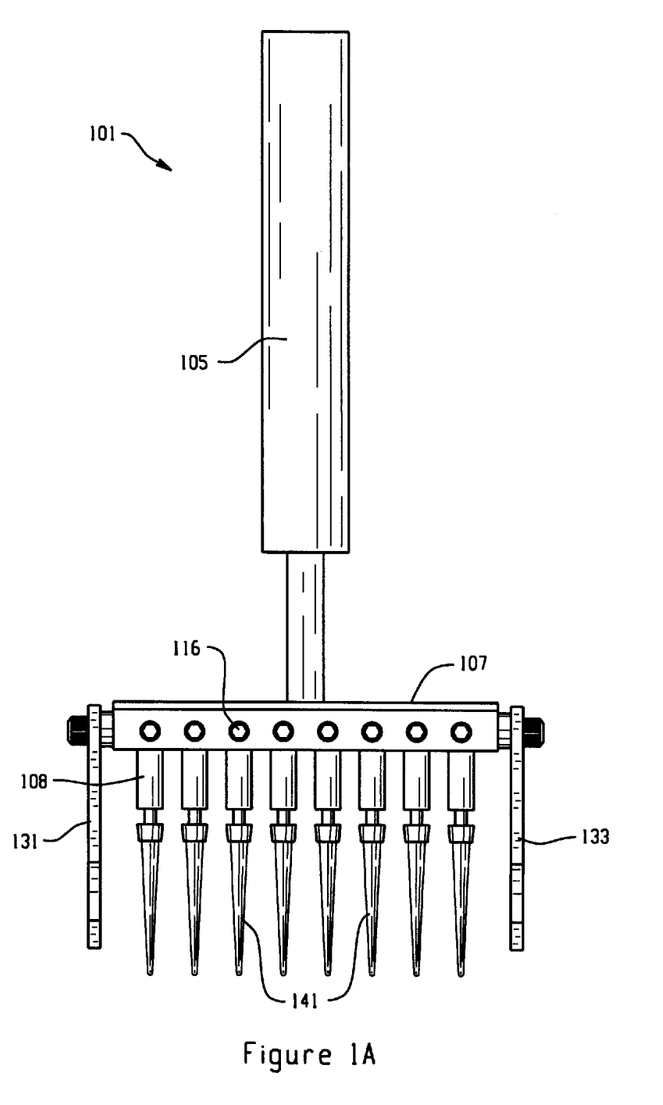

FIG. 1 (A) is a front view of an example eight-channel mechanical cellular wounder. In this embodiment the whole device (101) is made of stainless steel and can be sterilized by autoclaving. The handle (105) is permanently fixed at a perpendicular position to the pin holder (107). In this embodiment the pin holder consists of eight holes, and the pins (108) are inserted into each hole and held individually by the hex screws (116). The design of using 8 individually adjustable pins can ensure perfect contact of each tip (141) with the bottom of each well in a 96-well plate (not shown). This particular embodiment of the cellular wounder is tailor-made for 96-well plate format and the working angle of the two guiding-bars is also adjustable. There are two guiding-bars (131, 133) on the two sides of the pin holder and the working angle can be adjusted by the hex screws. These two bars help to position the pins at the central line of each well (not shown) and the bars ensure that the pins are located at the central line of each culture well. The depicted pins are designed to fit disposable p-10 pipette tips (141). Plastic pipette tips have several advantages including that the tips can provide enough elasticity to ensure perfect contact between the tips and the well surface (not shown), the smoothness of the tips causes no serious mechanical damages on the well surfaces, and the tips are inexpensive and are commercially available.

Figure 1B:
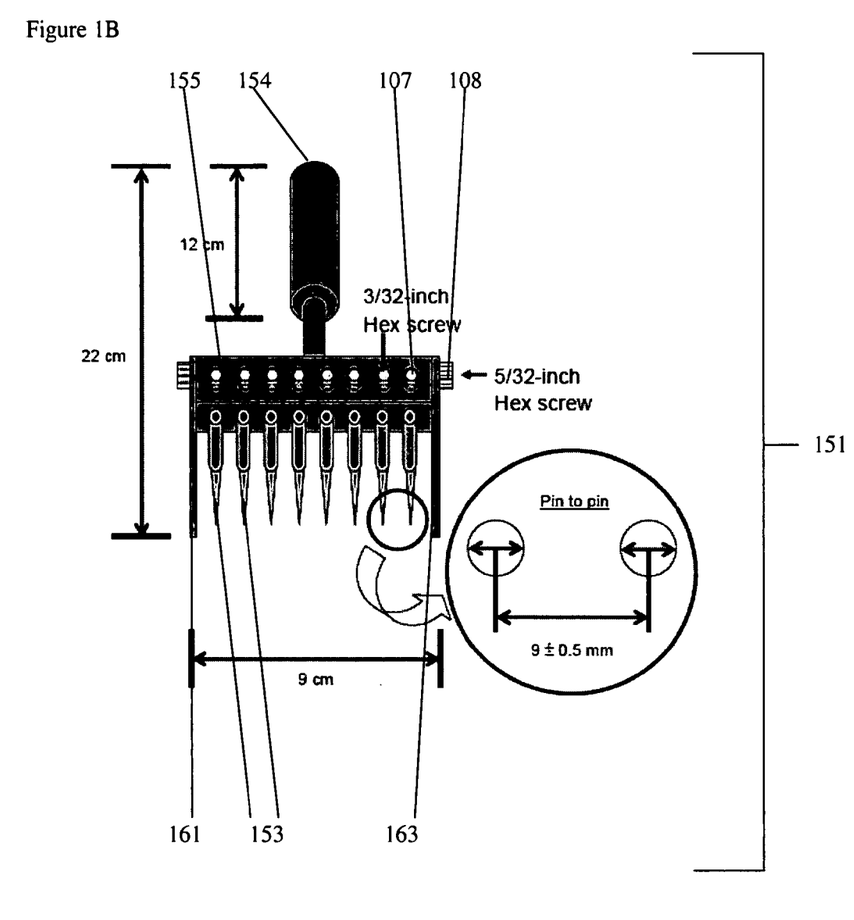

FIG. 1 (B) is a perspective view of an example eight-channel mechanical cellular wounder. The diagram shows the dimensions of one embodiment of the eight-channel mechanical cellular wounder (151). Each pin (153) is 3.5±0.1 mm in diameter and is designed to fit p-10 pipette tips such as Axygen and T-300 tips. Each pin is fixed on the pin holder (155) with distance of 9±0.5 mm (centre to centre). Pin length can be adjusted by length hex screw (107). The distance between the two guiding-bars (161, 163) is restricted to 8.2 cm, which is the width of a 96-well culture plate (not shown) such as a 3860-096 plate by Iwaki. The hex screws (108) on both edges of the pin holder are for adjustment of the guiding-bars. Handle (154) is made of a 12-cm long hollow stainless steel tube and autoclaved. The dimensions and device materials are provided by way of illustration only and can be varied without departing from the spirit and scope of the claimed invention.

Figure 2:
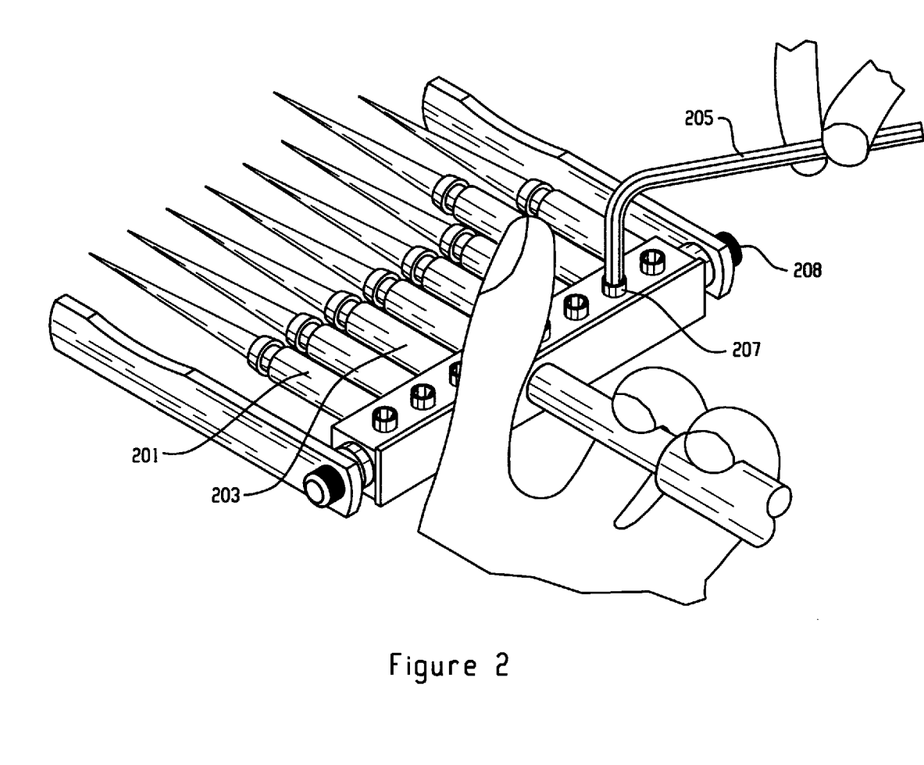
FIG. 2 is an alternate perspective view of the adjustment of the cellular wounding pins.

FIG. 2 is an alternate perspective view of the adjustment of the cellular wounding pins. Before wounding, p-10 pipette tips are fitted onto the pins and the level of each pin can be adjusted by the hex screws (207) using a hex wrench (205). This design, combined with the elasticity of plastic tips, ensures perfect contact of the tips with the surface of culture well, resulting in an even and consistent wounding of the cell monolayer. During the adjustment of the cellular wounding pins (201, 203), the protruded length of each pin can be adjusted using the hex wrench (205) upon the length adjusting screws (207). These fine adjustments ensure same extension of each tip for even contact with the surface of the well (not shown). The tightness of the wounder to hold a 96-well plate can be adjusted by the hex screws (208).

Figure 3:
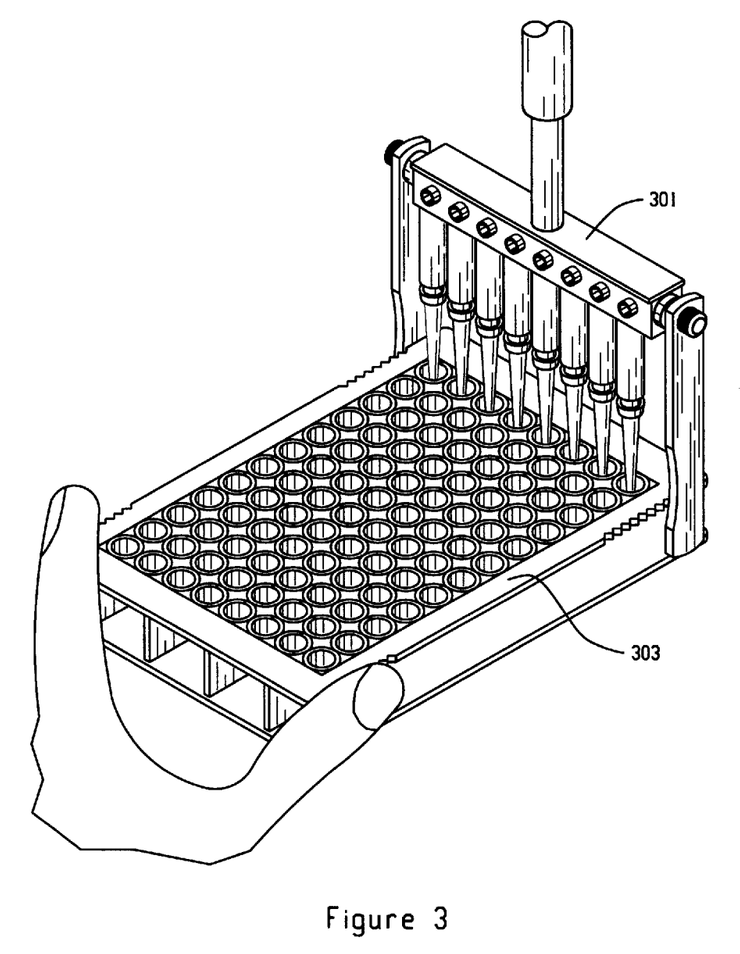
FIG. 3 is a side perspective view of the cellular wounder in use.

FIG. 3 is a side perspective view of the cellular wounder in use. The cellular wounder fitted with pipette-tips (301) is placed perpendicularly at the leftmost end of each well in the same column of the 96-well plate (303), then the cellular wounder is moved laterally to the rightmost end. The same procedure is repeated for all columns until all columns are scratched.

Figure 4A:
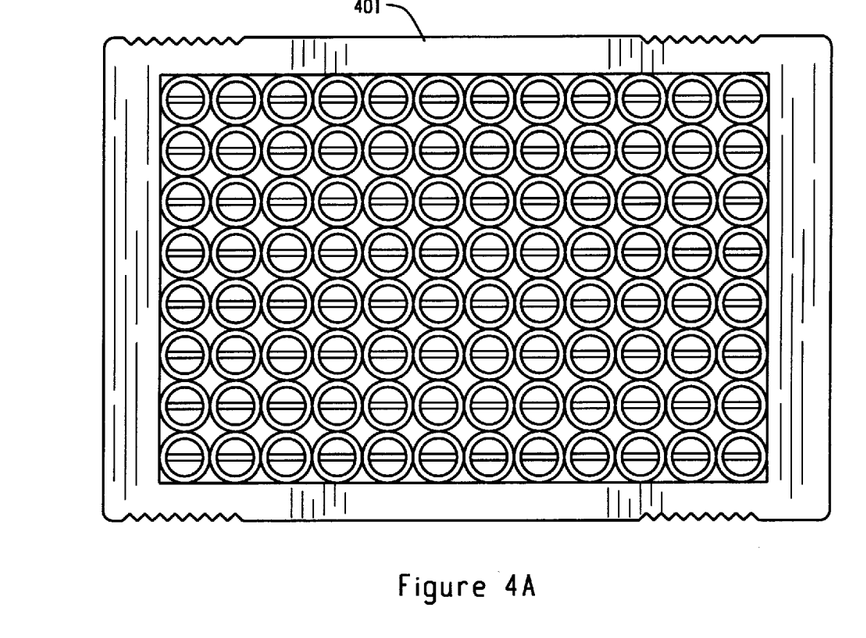

FIG. 4 (A) is a top view of a 96-well plate after application of the eight-channel mechanical cellular wounder. Performance of the eight-channel mechanical cellular wounder is measured for consistency of cell wounding size. FIG. 4(A) is a top view of the whole 96-well plate (401) after wounding. IEC-6 cells are seeded at a density of 4×10$^4$ onto the 96-well plate and incubated for a 24 hour period. Wounds are made by scratching with the eight-channel wounder (not shown) and after wounding, the cells are stained with Hemacolour 3 (not shown) to reveal a sharp wound visible in the centre of each well.

Figure 4B:
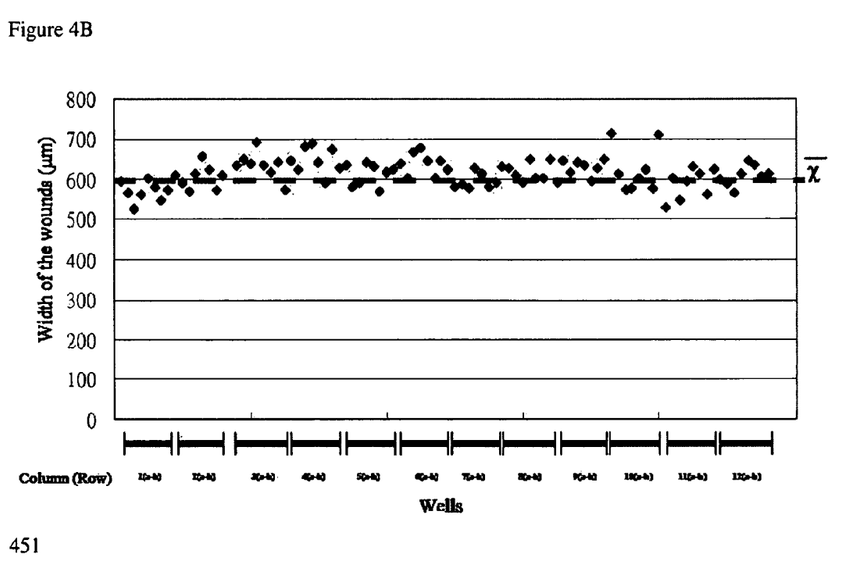

FIG. 4 (B) is a statistical representation (451) of wound size after device application. The width of each wound in each well is measured immediately after wounding in order to monitor the consistency. The average width of each wound in the 96-well plate is 600 μm with an SD of 36.6.

Figure 5A:
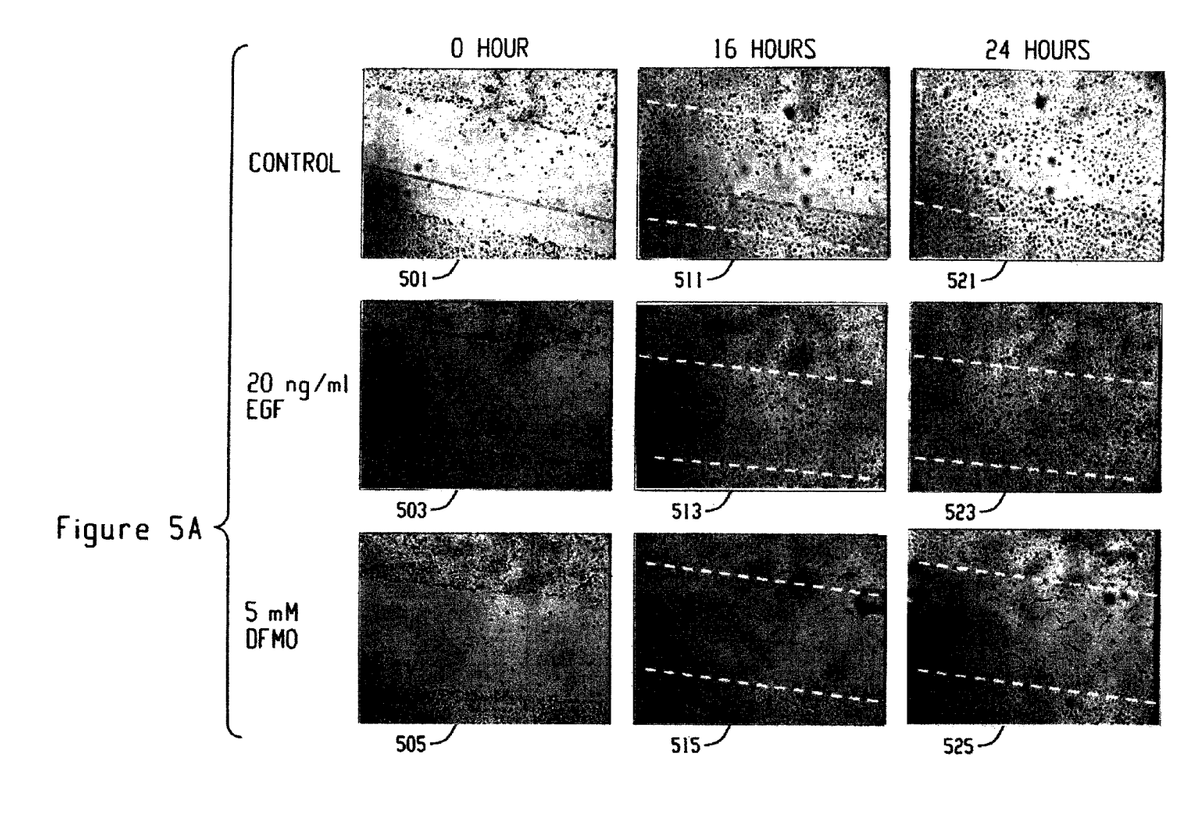

FIG. 5 (A) is a top view of migration of IEC-6 cells after cellular wounding. Wounded IEC-6 cells are treated with or without EGF (20 ng/ml) or DFMO (5 mM) for 24 hours. Photomicrographs of wounds are taken at time zero (501, 503, 505), 16 hours (511, 513, 515) and 24 hours (521, 523, 525) after wounding. Images at time zero are taken to record the initial width of the wounds and the recovery of the wounded monolayers due to cell migration towards the denuded area can be evaluated at 16 and 24 hours. The images are captured using an inverted phase-contract microscope such as a TMS Nikon with 4× objective, and the width of wound can quantified by the software such as Motic image plus 2.0 software of Motic Instruments. The migration of cells towards the wounds is expressed as a percentage of wound closure where % of wound closure=$[(W_{t=0} - W_{t=16 \, or \, 24})/W_{t=0}] \times 100\%$ where $W_{t=0}$ is the width of wound measured immediately after scratching and $W_{t=16 \, or \, 24}$ is the width of wound measured 16 hours or 24 hours after scratching.

Figure 5B:
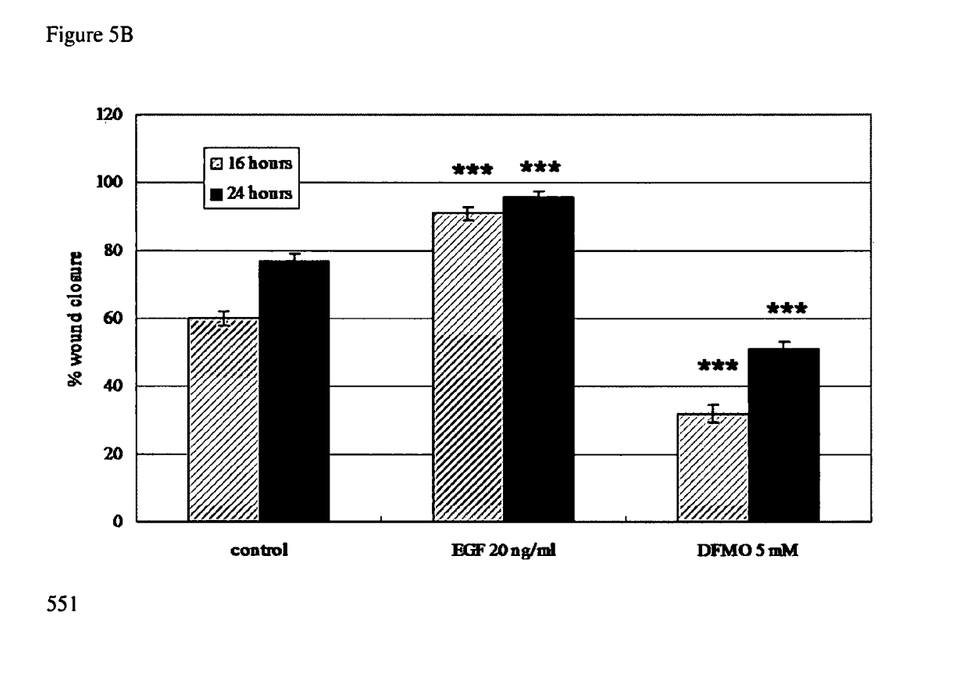

FIG. 5 (B) is a statistical representation (551) of cellular migration as a function of wound closure. Effects of EGF and DFMO on IEC-6 cells migration are plotted as % of wound closure. The results are expressed as mean±standard error of mean. *** $p<0.001$, relative to medium control.

Figure 6A:
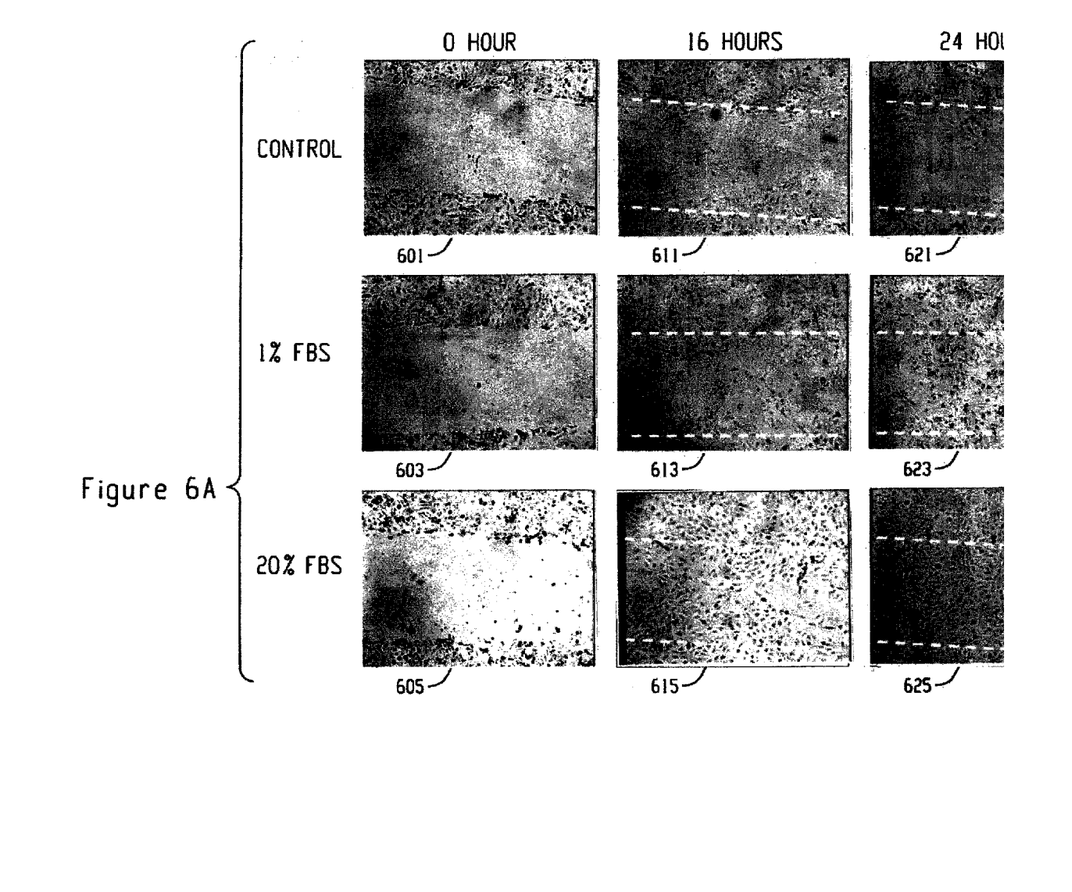

FIG. 6 (A) is a top view of migration of HUVECs after cellular wounding. Photomicrographs of wounded-HUVECs before and after FBS treatment. Wounded HUVEC are treated with various concentrations of FBS (0%, 1% and 20%) for 24 hours and photomicrographs of wounds are taken at time zero (601, 603, 605), 16 hours (611, 613, 615) and 24 hours (621, 623, 625) after wounding.

Figure 6B:
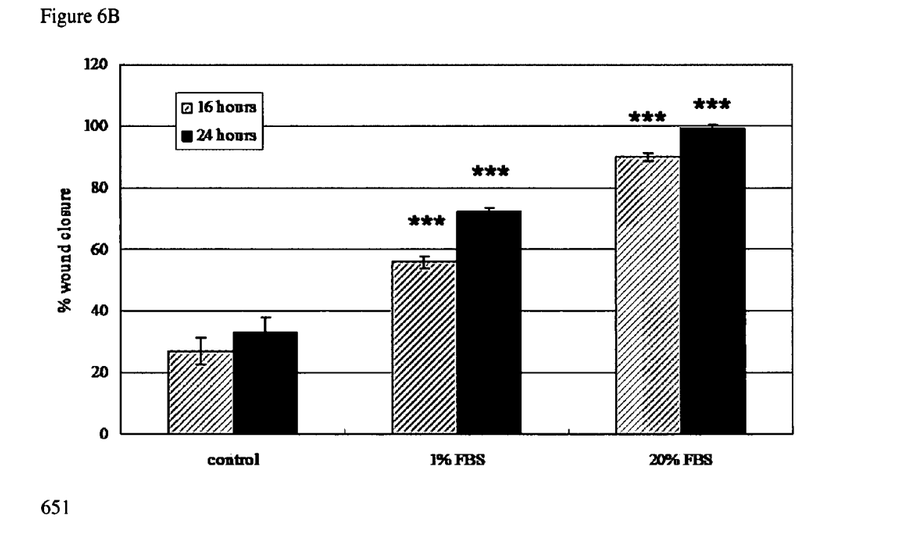

FIG. 6 (B) is a statistical representation (651) of cellular migration as a function of wound closure. The effect of FBS on HUVEC migration is plotted as % of wound closure. The results were expressed as mean±standard error of mean. *** $p<0.001$, relative to medium control.

INDUSTRIAL APPLICABILITY

The disclosed device and related method have industrial applicability in the life sciences and biomedical arts. The disclosed device and related method provide economies of scale and standardization in cellular manipulation.

We claim:

1. A device for uniform cellular manipulation comprising
    a handle,
    a pin holder,
    a plurality of pins, and
    a first adjustable guiding bar having a first end and an opposite second end, and connected onto a first side of the pin holder at its first end with a first adjustable screw such that the first guiding bar is orthogonal to the pin holder's length, and
    a second adjustable guiding bar having a first end and an opposite second end, and connected onto a second side of the pin holder at its first end with a second adjustable screw such that the second guiding bar is orthogonal to the pin holder's length, wherein the second side of the pin holder being opposite to the first side of the pin holder;
    wherein each of the guiding bars is rotationally adjustable with full rotation about at its first end independent of the other guiding bar by adjusting each of the screws such that each of the guiding bars having an independent working angle; and
    wherein said guiding bars are separated by a distance corresponding approximately to a width of a well plate and configured to hold onto the well plate by the second ends of the guiding bars with lateral force pressing against two opposing sides of the well plate.

2. The device of claim 1 wherein said pin holder additionally comprises length adjustable screws for varying the length of said pins.

3. The device of claim 1 wherein said pin holder additionally comprises width adjustable screws for adapting 96-well plate from different brands.

4. The device of claim 1 wherein said pins are adapted to receive standard disposable pipette tips.

5. The device of claim 1 wherein said device is made of stainless steel.

6. The device of claim 1 wherein said device contains eight pins spaced for use with a 96-well plate.

7. A single piece device for cellular wounding comprising
a handle,
a pin holder,
a plurality of length adjustable pins, and
a first adjustable guiding bar having a first end and an opposite second end, and connected onto a first side of the pin holder at its first end with a first adjustable screw such that the first guiding bar is orthogonal to the pin holder's length, and
a second adjustable guiding bar having a first end and an opposite second end, and connected onto a second side of the pin holder at its first end with a second adjustable screw such that the second guiding bar is orthogonal to the pin holder's length, wherein the second side being opposite to the first side of the pin holder;
wherein each of the guiding bars is rotationally adjustable with full rotation about at its first end independent of the other guiding bar by adjusting each of the screws such that each of the guiding bars having an independent working angle; and
wherein said guiding bars are separated by a distance corresponding approximately to a width of a well plate and configured to hold onto the well plate by the second ends of the guiding bars with lateral force pressing against two opposing sides of the well plate.

8. The device of claim 7 wherein said device is made of a material which is capable of withstanding heat sterilization.

9. The device of claim 7 wherein said device is made of stainless steel.

10. The device of claim 1 wherein tightness of the device to hold on the well plate is accomplished by adjusting the screws.

11. The device of claim 7 wherein the adjustment of each of the guiding bars wherein tightness of the device to hold on the well plate is accomplished by adjusting the screws.

12. The device of claim 1 wherein said guiding bars are separated by a distance corresponding approximately to a width of a 96-well plate and configured to hold onto the 96-well plate.

13. The device of claim 7 wherein said guiding bars are separated by a distance corresponding approximately to a width of a 96-well plate and configured to hold onto the 96-well plate.

14. The device of claim 1 wherein each of said guiding bars is rotated at its first end to ensure each of the pins is located at a central line of a well held by the well plate.

15. The device of claim 7 wherein each of said guiding bars is rotated at its first end to ensure each of the pins is located at a central line of a well held by the well plate.

* * * * *